United States Patent [19]

DeBonte et al.

[11] Patent Number: 5,066,594

[45] Date of Patent: Nov. 19, 1991

[54] METHOD FOR THE MANIPULATION OF POLLEN IN PLANTS

[75] Inventors: Lorin R. DeBonte, Delran, N.J.; Willie H. T. Loh, Philadelphia, Pa.

[73] Assignee: DNA Plant Technology, Cinnaminson, N.J.

[21] Appl. No.: 349,570

[22] Filed: May 9, 1989

[51] Int. Cl.$^5$ .......................... C12N 5/02; C12N 5/04
[52] U.S. Cl. ...................... 435/240.4; 435/172.3; 435/240.46; 47/58; 47/DIG. 1
[58] Field of Search ............ 435/172.3, 240.4, 240.46; 47/58, DIG. 1

[56] References Cited

PUBLICATIONS

Ohta, (1986) Proc. Mat. Acad. Sci. U.S.A., vol. 83, pp. 715–719.
Fromm et al. (1986) Nature., vol. 319, pp. 791–793.
Saini et al. (1986) Maydica, vol. 31(2), pp. 227–232.
Pfaliler et al. (1980) Con. Jour. Botany, vol. 58(5) pp. 557–561.
Sinha (1972/73) Progressive Hort. 4(3/6) pp. 45–52.
Ferrari et al. (1975) Euphytica 24(3) pp. 757–765.
Dupuis et al., 1987, Plant Physiol. 85:876–878.
Dhingra and Varghese, 1985, Ann. Bot. 57:101–104.
Dhingra and Varghese, 1985, Ann. Bot. 55:415–420.
Roberts et al., 1983, Theor. Appl. Genet. 65:231–238.
Hong-Qi and Croes, 1982, Acta Bot. Neerl. 31:113–119.
Pfahler et al., 1982, Acta Bot. Neerl. 31:105–111.
Portnoi and Horovitz, 1977, Ann. Bot. 41:21–27.
Goss, 1968, Bot. Rev. 34:333–358.
Pfahler, 1967, Can. J. Bot. 46:235–240.
Pfahler, 1967, Can. J. Bot. 45:839–845.
Cook and Walden, 1967, Can. J. Bot. 45:605–613.
Brewbaker and Dwack, 1963, Am. J. Bot. 50:859–865.

*Primary Examiner*—Elizabeth C. Weimar
*Assistant Examiner*—Gary Benzion
*Attorney, Agent, or Firm*—Pennie & Edmonds

[57] ABSTRACT

The present method is directed to a method for the in vitro stabilization and manipulation of pollen from flowering plants. Specifically, the in vitro stabilization method comprises stabilizing germinating pollen in an aqueous stabilizing solution. The growth of the pollen tube may be resumed by suspending the stabilized pollen in germination medium. Stabilized pollens may be used as vectors for the transfer of exogenous DNA into plants or in gametophyte selection.

41 Claims, No Drawings

METHOD FOR THE MANIPULATION OF POLLEN IN PLANTS

TABLE OF CONTENTS

1. Field of the Invention
2. Background of the Invention
   2.1. In Vitro Germination of Pollen
   2.2. Transfer of Exogenous DNA Into a Flowering Plant
3. Summary of the Invention
4. Detailed Description of the Invention
   4.1. In Vitro Germination of Pollen
   4.2. Pollen Mediated Transfer of Exogenous DNA Into Flowering Plants
5. Examples
   5.1. Example 1: In Vitro Germination of Maize Pollen

1. FIELD OF THE INVENTION

The present invention relates to an in vitro method for the stabilization and manipulation of pollen in flowering plants. Specifically, the method involves the stabilization of pollen after germination. This method may be used to germinate pollen in a variety of flowering plants with relatively high viabilities. Such a method may have use in the transfer of exogenous deoxyribonucleic acid (DNA) fragments into flowering plants or in gametophyte selection.

2. BACKGROUND

2.1. In Vitro Germination of Pollen

Pollen in flowering plants is generally produced in staminate flowers. In corn, for example, such staminate flowers occur in clusters (the tassel) at the top of the plants (reviewed in Goss, 1968, Bot. Rev. 34:333-358). Three stamens are formed within each flower with elongated anthers that open at the tips following anthesis. During meiosis, microspores are produced in the anthers which subsequently develop into pollen grains. Such pollen grains are released and dispersed by the wind. As a result, self-pollination, and/or cross-pollination may occur. During pollination, the pollen grains are caught on stigmas of the pistillate flowers which are borne in clusters lower on the plant which make up corn silk and begin to germinate within one to one and a half hours. Pollen tubes are usually well established in the corn silks two hours after pollination.

Pollen produced, however, must be viable for a long enough period of time for pollination to occur. Therefore, studies of pollen viability are of great practical as well as theoretical value. Environmental conditions may adversely affect pollen viability and, ultimately, fertilization due to the transportation of pollen for breeding purposes over long distances. Furthermore, pollen is not always produced at the time or place where needed for plant breeding studies.

During pollen grain development, the maize microspore divides to form the generative and tube nuclei. The generative nucleus divides again to produce two crescent-shaped sperm cells. Thus, the pollen grain of maize has three nuclei (trinucleate) when released from the anther. Brewbaker and Majumbder (1959, Adv. Bot. 1:1503-1508) showed that whereas binucleate pollen grains germinate very well. Other agronomic crops with trinucleate pollen include Brassica (vegetable and oilseed rape) and Triticum (wheat).

Numerous studies have focused on the in vitro germination of pollen grains in a number of crops. Several factors may influence the in vitro germination of such a crop. These include the particular genotype which is being cultivated, how long the plant was stored after anthesis before obtaining the pollen, and the composition of the media. Procedures used in the art generally involve incubating the pollen grains on a solid substrate (e.g. agar) containing a given culture medium until there is a profusion of pollen tubes from germination pores (reviewed in Goss, 1968, Bot. Rev. 34:333-358). There is a general consensus that calcium, boron, and an osmoticum are critical in obtaining pollen germination in a variety of flowering plants, examples which include corn (Cook and Walden, 1967, Can. J. Bot. 45:605-613; Pfahler, 1968, Can. J. Bot. 46:235-240; and Goss, 1968, Bot. Rev. 34:333-358), Brassica (Roberts et al., 1983, Theor. Appl. Genet. 65:231-238), and petunia (Brewbacker et al. 1963, Am. J. Bot. 56:861-865). The osmoticum generally used is a sugar. (Goss, 1968, supra and Portnoi et al., 1977, Ann. Bot. 41:21-27). The most frequently used sugar when germinating pollen in vitro is sucrose.

The effects of other substances on in vitro germination of pollen has also been tested. For example, polyethylene glycol-400 (PEG-400) has been proposed as a substitute for sugar for germinating Petunia pollen since it is not easily metabolized in pollen (Hong-Qi and Croes, 1982, Acta Bot. Neerl. 31:113-119). PEG was found to promote tube growth considerably more than a medium containing sucrose. The effect of gibberelins on in vitro germination of various species of corn was also determined (Pfahler et al., 1982, Acta. Bot. Neerl. 31:105-111). The results from these studies indicate that any stimulating effect that $GA_3$ has is largely genotype specific. The utility of the following nonionic surfactants, Tween 80 (polyoxyethylene sorbitan monooleate), X-114 (alkyl phenoxy-polyethoxy ethanol), and commercial sticker spreader (alkyl olefin aromatic polymers) in combination with a known germination medium (sucrose, bacto-agar, $Ca(NO_3)_2$ and boric acid was studied (Pfahler et al., 1980, Can. J. Bot. 58:557-561). It was found that the more nonionic surfactant, X-114, had the greatest effect on germination.

Results from previous studies indicate that lysis of the pollen cell wall occurs immediately when corn pollen grains are incubated in pollen germination medium which does not contain agar (reviewed in Goss, 1968, Bot. Rev. 34:333-358). Ultimately, the bursting of the pollen and the release of DNAses will follow. A new medium containing calcium, boron, lysine, a glutamic acid, and sucrose was disclosed and said to overcome the problems typically encountered with corn pollen lysing and germination (Saini et al., 1986, Maydica XXXI:227-232). Pollen was incubated in the medium for 15-23 minutes and then stored in an oven at 24° C. for varying lengths of time. The best results were obtained with pollen grains which had been stored 12 hours after anthesis. The germination rate was 60% and after germination could be stored for up to 7.5 hours before bursting. Pollen grains which were germinated at the time of anthesis had a germination rate of 75% but burst after a 5 hour storage period.

Dupuis et al. (1987, Plant Physiol. 85:876-878), isolated viable sperm cells from maize pollen grains. The pollen grains were germinated in a solution which induced lysis to release the pollen contents. No pollen tube growth was observed prior to lysis.

Finally, studies have been conducted to determine the effect of salt on the viability of maize pollen (Dhingra et al., 1985, Ann. Bot. 55:415-420 and Dhingra and Varghese, 1986, Ann. Bot. 57:101-104). The viability and germination of maize pollen was found to be adversely affected by relatively high levels of salinity (e.g. 160 mg/l). In addition, an increase in amylase and invertase activities was observed with increasing salinity resulting in a greater proportion of soluble sugars. Such sugars may be used as respiratory substrates, which may ultimately alter the viability of the pollen.

2.2. Transfer of Exogenous DNA Into a Flowering Plant

With the advent of genetic engineering, it has become a major goal to modify and improve plants by introducing foreign genes encoding important functional traits. Such traits might include resistance to herbicides, pesticides, or pests; tolerance to cold, heat, drought, or salinity; or improved nutritional quality or yield of specific plant products. The current population explosion and concomitant world food and fiber shortage demand improved productivity in agricultural efforts since virtually all of the readily available, relatively fertile cropland in developed countries has already been placed in use (Barr, Science, 1981, 214:1087-1089). Modification of monocotyledonous plants including the cereals and many food crops would provide major nutritional and economic benefits.

A number of approaches currently exist for transferring heterologous gene(s) or gene sequences(s) into the genome of plants, also known as plant transformation. The first, (Chilton et al., 1977, Cell 11:263-271) relies on infection by Agrobacterium bacteria, which inserts sequences of a plasmid, known as the Ti-plasmid, into the genome of plant cells. Agrobacterium mediated plant transformation has been less successful in monocots then dicots. Integration of T-DNA has been demonstrated in only a few non-regenerable monocot systems, namely, Chlorophytum and Narcissus (Van Slogteren et al., 1984, Nature 311:763-764) and Lolium (Potrykus et al., 1985, Mol. Gen. Genet. 199:183-188). At the present time, this approach is not considered useful in transformation of major monocot crops, i.e. corn, wheat, rice, etc.

A second approach, known as direct transformation, induces uptake and integration of plasmid or linearized DNA into the genome of plant protoplasts, i.e. single cells stripped of cell wall material (Lorz et al., 1985, Mol. Genet. 199:178-182). When protoplasts and DNA molecules are incubated together, under proper inducing conditions (i.e. the use of polyethylene glycol, liposomes and/or electroporation), DNA is taken up and integrated into the plant genome. The frequency of transformation is highly variable, however, and very few major crop plants can be regenerated from protoplasts.

Another approach involves the transfer of exogenous bacteriophage or plasmid DNA into germinating pollen grains to modify plant properties. As the pollen tube emerges from the mature pollen grain, cell wall material is deposited behind the growing tip. Therefore, immediately behind the growing point, the cell wall is just beginning to form. Exogenous DNA may be able to enter the male gametophyte, and be carried to the egg during the course of pollen tube growth and fertilization. Examples of such pollen-mediated DNA transfer are detailed infra.

A series of papers by Dieter Hess report plant transformation through uptake of intact bacteriophages into germinating pollen. Experiments were described in which Petunia hybrid pollen was treated with lac-transducing phages (Hess, 1978, Z. Pflanzinphysiol. 90:119-132). Progeny derived from the treated pollen showed improved growth on lactose media. Similar results were obtained by treating Petunia pollen with gal transducing phages (Hess, 1979, Z. Pflanzingphysiol. 93:429-436). The transduction frequency however was very low.

DeWet (PCT Patent Application WO 85/01856, 1985) discloses a method for transferring genes between maize inbreds using pollen as a vector comprising the steps of (a) obtaining DNA from a selected donor plant and optionally placing said DNA in a buffer and/or storing it; (b) removing mature pollen from a chosen pollen-donor plant; (c) germinating the pollen; (d) incubating the germinated pollen with the donor DNA; (e) pollinating the pollen-donor plant or other compatible mother plants with the treated pollen; (f) harvesting the resultant seed from the plant; and (g) germinating the seed and screening for transformed plants. The method is quite inefficient as demonstrated for maize, however, in that the majority of ears receiving DNA-treated pollen produced no caryopses and only 1 to 5 well developed caryopses developed per influorescence pollinated in those ears which set seed. The maximum number of caryopses produced was 50 per influorescence, compared to between 300 and 500 caryopses following pollination with untreated pollen. In addition, only about 24 percent of the caryopses resulting from the DNA-treated pollen germinated while about percent of untreated caryopses germinated.

Another method for the transformation of Zea mays involves the self-pollination of plants with pollen which had been incubated with DNA prepared from plant leaves of a corn strain carrying dominant alleles for a set of markers for which the recipient has recessive alleles (Ohta, 1986, Proc. Natl. Acad. Sci. U.S.A. 83:715-719). The high molecular weight DNA was suspended in 0.3M sucrose at a concentration of 40 $\mu$g/ml, and added to fresh pollen from a recipient plant to make a pasty DNA/pollen mixture. The mixture was then laced on the silks of the recipient plant for self-pollination. Maize plants pollinated with the DNA/pollen mixture immediately after it was made produced an average of 135.8 kernels per ear, compared to 146.1 kernels per ear for ears pollinated normally. Phenotypically different kernels were found on four of eight ears to which the mixture was applied. If as little as 5 min. elapsed between the time of preparing the DNA/pollen mixture and placing it on the silks, seed set was drastically reduced and no variant kernels were obtained. About 3.2 percent of the kernels from ears which were pollinated with DNA treated pollen were phenotypically different. Among the variant kernels which germinated, none of the traits segregated as expected in the subsequent generation. Ohta also utilized a procedure whereby the DNA was applied directly to the silk followed by self-pollination. Ears receiving exogenous DNA in this manner showed greatly reduced seed set (3 kernels from 5 ears) and none of them were phenotypically different.

A third method involving pollen mediated transfer of exogenous DNA into Zea mays is disclosed in EPO Application No. 0275,069, published July 20, 1988, comprising the steps of: (a) suspending a DNA construct incorporating the exogenous DNA fragment, in a delivery medium which comprises polyethylene glycol and proteinase K; (b) contacting the pollen-receptor organs of the plants with the suspension of step (a); and (c) contacting the pollen-receptor organs with related ungerminated pollen within a period of less than 5 minutes after step (b). In an example described in the disclosure, the transformation of the genes encoding kanamycin resistance into maize pollen was significantly higher using the disclosed method than when the gene was transformed into maize pollen using the procedure described by DeWet in PCT Patent Application WO 85/01856.

An attempt has also been made to introduce a plasmid encoding kanamycin resistance into mature germinating tobacco pollen (Negrutiu et al., 1986, in: Biotechnology and Ecology of Pollen, eds. D. L. Mulcahy, G. Bergamine, and E. Octavians, Springer Verlag, New York, pp. 65-69). Tobacco pollen was germinated in the presence of the vector DNA, and various procedures, including heat shock, polyethylene glycol, and electroporation, were employed to induce uptake. Following pollination with the treated pollen, the resulting seeds were collected, germinated and screened for kanamycin resistance. A total of 400,000 seeds were screened but no resistant seedlings were found. The author speculated that the failure was due to the poor uptake of the DNA and/or degradation of the DNA once it was in the pollen tube.

A second method for introducing exogenous DNA into Nicotiana has been disclosed (PCT Application Publication No. WO89/00602, published Jan. 26, 1989 and Alwen, Abstract, International Plant Molecular Biology Congress, Jerusalem, Israel, Nov. 13-18, 1988). This method specifically involves: (a) removing unripe pollen grains from the stamens and placing them in a nutrient solution; (b) culturing the isolated unripe pollen grains in nutrient solution; (c) transferring exogenous genetic material to the pollen grains during the in vitro culture step via e.g. electroporation microinjection Agrobacterium infection; (d) incubating the ripening pollen with the exogenous genetic material until fully ripe; and (e) pollinating the pollen-donor plant or other compatible mother plants with the treated pollen. Results from preliminary studies indicate that electroporation and microinjection may lead to pollen death, but that pollen transformation by Agrobacterium may occur.

3. SUMMARY OF THE INVENTION

The present invention provides a novel method for the in vitro stabilization of germinating pollen in flowering plants which comprises stabilizing the germinating pollen in an aqueous stabilization solution, thereby suspending the growth of the pollen tube. The stabilization medium comprises effective amounts of polyethylene glycol, a salt, and an osmoticum.

The stabilized pollen may be suspended in a solution of pollen germination medium to resume the growth of the pollen tube. As will be shown in the examples described herein, higher viabilities of maize pollen has been observed using the method of the present invention than when using other procedures known in the art.

The method of the present invention may also have use in the pollen-mediated transfer of exogenous deoxyribonucleic acid (DNA) fragments into flowering plants. Specifically the method may be used to improve the methods disclosed in the art for pollen mediated transfer of exogenous plasmid DNA (DeWet PCT application 85/01856, 1985; and which disclose methods Negrutiu et al., 1986, in: Biotechnology and Ecology of Pollen, eds. D. L. Mulcahy, G. Bergamine and E. Octavians, Springer Verlag, New York, pp. 65-69) or for the uptake of intact bacteriophages into germinating pollen (Hess et al., 1978 Z. Pflanzenphysiol. 90: 119-132 and Hess et al., 1979, Z. Pflanzenphysiol. 93: 429- 436). Such an improvement would comprise, after germinating the pollen in pollen germination medium, stabilizing the germinated pollen in aqueous stabilizing solution, and incubating the donor DNA with the stabilized pollen for up to one hour. The method of the present invention may also be used in gametophyte selection.

4. DETAILED DESCRIPTION OF THE INVENTION

The present invention provides a method for the in vitro stabilization and manipulation of pollen from flowering plants. The in vitro stabilization method comprises stabilizing germinating pollen in an aqueous stabilizing solution containing effective amounts of polyethylene glycol, a salt and an osmoticum. The growth of the pollen tube may be resumed by suspension in germination medium. The viability of pollen stabilized in vitro using the present method of the invention is higher than if the pollen was germinated using procedures known in the art. Pollen germinated by this method may be used as vectors for the transfer of exogenous DNA into plants and would provide an improvement over the procedure disclosed in the art (DeWet, 1985, supra; Negrutiu, 1986, supra; and Hess, 1978, 1979, supra). In another embodiment, pollen which is germinated and stabilized using the method of the present invention, may be used in gametophyte selection.

Other methods for pollen mediated transformation of maize include microprojectile bombardment, laser microinjection and physical microinjection. Stabilization of germinated pollen would expose the sperm nuclei and improve the success rate of all these methods.

4.1. In Vitro Germination of Pollen

The in vitro germination method of pollen of the present invention may be divided into the following general stages for the purposes of description: (a) washing the germinated pollen with a stabilization solution; (b) separating the pollen from the stabilizing solution; and (c) resuspending the pollen in stabilization solution. The pollen may be obtained from flowering plants, which may include but are not limited to corn, rice, wheat, sugar beet, tomato, clover, tobacco, arabidopsis, soybean and Brassica. The pollen may also be obtained from flowering plants that contain trinucleate pollen. The procedures and principles involved in the germination of the pollen are well known in the art and are discussed generally in Goss, 1968, (Bot. Rev. 34:333-358). The present method is not in any way limited to use of a particular method of pollen germination. A typical pollen germination medium comprises calcium, boron and an osmoticum with an effective osmolarity of 0.29 osmols. A particularly useful combination comprises using about 5-20% sucrose, 0.5 mM-5 mM calcium nitrate, and 0.3-3 mM borate. The combination of the components in the stabilization solution apparently serve to prevent the bursting of the cell wall, resulting in the release of DNAses and the lysis of the pollen. Such a problem is usually observed using other procedures known in the art when pollen is incubated in solution.

The stabilization solution in one embodiment, comprises effective amounts of polyethylene glycol of a molecular weight of about at least 800 (5-15%), sodium chloride (70-200 mM), and an osmoticum with an effective osmolarity of 0.15-0.58 osmols. The osmoticum may comprise a sugar or sugar alcohol which may include but is not limited to dextrose, galactose, glucose, fructose, mannose, ribose, sucrose, glucitol, mannitol, sorbitol, or threitol. A particularly useful combination comprises using effective amounts of polyethylene glycol of molecular weight of at least about 800 (5-15%), sodium chloride (70-200 mM), an osmoticum with an effective osmolarity of 0.29 osmols., calcium (e.g., calcium acetate, calcium chloride, or calcium nitrate; 0.5 mM-5 mM), boron (boric acid or sodium borate, 0.3 mM-3 mM), and potassium chloride (0.5 mM-5 mM). The pollen may be separated from the stabilization solution by centrifugation. The pollen is contained in the pellet. After resuspending the pollen in stabilization solution, the growth of the pollen tube may be suspended for up to about one hour. Resumption of growth of the pollen tube can be induced by resuspension in pollen germination medium after a second pelleting.

4. 2. Pollen Mediated Transfer of Exogenous DNA Into Flowering Plants

The method of the present invention may be of use in the pollen-mediated transfer of exogenous DNA into a flowering plant. As described in Section 2.2, supra, methods for pollen mediated transfer of exogenous plasmid DNA into Zea Mays DeWet, PTC Patent application WO 85/01856) and Nicotiana (Negrutiu et al., 1986, in: Biotechnology and Ecology of Pollen, eds. D. L. Mulcahy, G. Gergamini, and E. Ottavians, pp. 65-70) and the Transduction of bacteriophage DNA (Hess et al., 1978, Z. Pflanzinphysiol 90:119-132 and Hess et al., 1979, Z. Pflanzinphysiol. 93: 429-436).

The transformation efficiencies obtained using the methods known in the art are quite low. In the DeWet method, the majority of corn ears receiving DNA treated pollen produced no caryopses. In addition, in a preferred embodiment, pollination is initiated immediately after mixing the exogenous DNA with the pollen. No transformants were obtained using the method described by Negrutiu. Low transformation frequencies were also obtained when phage DNA was transduced into Petunia, using pollen as a vector (Hess, et al. 1978 and 1979, supra).

The methods known in the art for transferring exogenous DNA using pollen as a vector may be improved by stabilizing the germinating pollen. Pollen tube growth as described in Section 4.1., supra is suspended after washing with stabilization solution, centrifuging the suspension to separate the pollen from the stabilization solution, and resuspending the pollen containing pellet in stabilization solution. The exogenous DNA which is suspended in buffer at this time can then be added to the stabilized pollen. This DNA/pollen mixture can be incubated at 20° C.-30° C. for up to about one hour before initiating pollination. The DNA/pollen mixture may be placed on the silks of the recipient plant when working with corn. This improvement is more efficient than methods known in the art since more viable pollen will be produced. In addition, since the pollen can be manipulated for up to about 1 hour, the method is more flexible than DeWet and the transformation frequency should be higher.

5. EXAMPLES

5.1. Example 1: In Vitro Germination of Maize Pollen

The pollen is harvested from anthers located within 2 cm. on the same tassel to ensure the synchronicity of germination. The anthers should be emerging from the glumes. The pollen from 10 anthers is sprinkled onto a petri dish containing KYM (15% sucrose, 1.6 mM boric acid, 1.3 mM calcium nitrate) agar. The pollen is allowed to germinate at 25° C. for 10-25 minutes. The pollen tube should preferably not elongate more than one half of the pollen grain width if they are to be used for pollination, and may be observed microscopically. If not, the tube length is not critical.

Pollen is then washed free of KYM agar with 0.5 TB 3500 (10% sucrose, 10% PEG 3500, 1.3 mM calcium nitrate, 1.6 mM boric acid, 140 mM sodium chloride, and 26 mM potassium chloride). Such a treatment serves to stabilize the pollen tube and to inhibit DNAses. Once TB 3500 comes in contact with the germinating grains, the tubes stop elongating. Subsequently, the pollen is centrifuged at a relative centrifugal force (RCF) of 100 for 30 seconds. After pipetting off the supernatant, the pellet is suspended in TB 3500. The pollen is centrifuged again for 30 seconds at 100 RCF, and the supernatant is removed. The pellet is resuspended in 0.5 KYM liquid and pipetted over KYM agar. At this point, pollen tube growth should resume.

Viability of pollen was determined microscopically at the germination stage, after the addition of TB 3500, the second wash of TB 3500, and after the resuspension of pollen in KYM (Table I). The treatments were scored for length of pollen tube, rate of cytoplasmic streaming, and percent lysis. The length of the pollen tube is compared to the pollen grain diameter, 1X is equal to the diameter. The time elapsed from the start of germination at each observation is also recorded. Experiments are initiated only if greater than 70% of the pollen grains germinate by 20 minutes.

TABLE I

| | Results of Viability Test | | | |
|---|---|---|---|---|
| Stage of Treatment | Time From Germination | Length of Pollen Tube | Cytoplasmic Streaming | Lysis (%) |
| Germination | 20 min. | ½ X | rapid | 0 |
| TB Wash 1 | 35 min. | ½ X | reduced | 5 |
| TB Wash 2 | 100 min. | ½ X | reduced | 10 |
| KYM Resusp. | 115 min. | 1 X | rapid | 10 |
| KYM Resusp. | 135 min. | 5 X | rapid | 20 |

The pollen has been held in TB 3500 at 25° C. for two hours with resumption of growth. Periods longer than this have not been tried. Once the pollen is resuspended in the KYM on KYM agar plates it will continue growth for five hours.

What is claimed is:

1. A method for stabilizing a germinated pollen grain from a flowering plant which comprises treating a pollen grain bearing a growing pollen tube with an aqueous stabilization medium comprising amounts of polyethylene glycol, a salt, and an osmoticum effective in combination to suspend further growth of the pollen tube for a time up to about 2 hours sufficient to manipulate the pollen grain, after which time, upon removal of the pollen grain from the stabilization medium, the growth of the pollen tube can be resumed.

2. The method according to claim 1 in which the flowering plant contains trinucleate pollen.

3. The method according to claim 1 in which the flowering plant is selected from the group consisting of corn, rice, wheat, sugar beet, tomato, clover, tobacco, arabidopsis, soybean, and Brassica species.

4. The method according to claim 1 in which the polyethylene glycol has a molecular weight of at least about 800.

5. The method according to claim 1 in which the salt is selected from the group consisting of sodium chloride, potassium chloride, sodium phosphate, potassium phosphate, and calcium chloride.

6. The method according to claim 1 in which the osmoticum is selected from the group consisting of a sugar or sugar alcohol.

7. The method according to claim 6 in which the sugar or sugar alcohol is selected from the group consisting of dextrose, galactose, glucose, fructose, mannose, ribose, sucrose, glucitol, mannitol, sorbitol, or threitol.

8. The method according to claim 1 in which the aqueous stabilization solution comprises about 5–15% polyethylene glycol, 70–200 mM NaCl, and 5–20% sucrose.

9. The method according to claim 1 in which the aqueous stabilization medium further comprises calcium and boron.

10. The method according to claim 9 in which the calcium is selected from the group consisting of calcium acetate, calcium chloride or calcium nitrate.

11. The method according to claim 9 in which the boron is selected from a group consisting of boric acid and sodium borate.

12. The method according to claim 9 in which the aqueous stabilization solution comprises about 5–15% polyethylene glycol, 70–200 mM sodium chloride, 5–20% sucrose, 0.5 mM–5 mM calcium nitrate, 0.3 mM–3 mM sodium borate, and 0.5 mM–5 mM potassium chloride.

13. The method according to claim 1 in which the growth of the pollen tube may be resumed by suspending the stabilized pollen in a solution of pollen germination medium.

14. The method according to claim 13 in which the stabilized pollen is suspended in aqueous pollen germination medium comprising an osmoticum, boron, and calcium.

15. The method according to claim 14 in which the osmoticum is selected from the group consisting of a sugar or sugar alcohol.

16. The method according to claim 15 in which the sugar or sugar alcohol is selected from the group consisting of dextrose, galactose, glucose, fructose, mannose, ribose, sucrose, glucitol, mannitol, sorbitol, or threitol.

17. The method according to claim 14 in which the calcium is selected from the group consisting of calcium acetate, calcium chloride or calcium nitrate.

18. The method according to claim 14 in which the boron is selected from a group containing boric acid or sodium borate.

19. The method according to claim 14 in which the pollen germination medium comprises 5–20% sucrose, 0.5 mM–5 mM calcium nitrate, and 0.3 mM–3 mM borate.

20. An in vitro method for stabilizing a germinated pollen grain from a flowering plant for a time sufficient to manipulate the pollen grain, and subsequently resuming germination of the pollen grain, which comprises:

(a) washing a germinated pollen grain bearing a growing pollen tube with an aqueous stabilization medium comprising amounts of polyethylene glycol, a salt, and an osmoticum effective in combination to suspend further growth of the pollen tube;

(b) separating the washed stabilized pollen grain of step (a) from the stabilization medium by centrifugation to yield a pellet containing the stabilized pollen grain;

(c) resuspending the pellet in step (b) in the stabilization medium to step (a) for a time up to about 2 hours sufficient to manipulate the pollen grain;

(d) separating the resuspended stabilized pollen grain of step (c) by centrifugation to yield a pellet containing the stabilized pollen grain; and (e) resuming the germination of the pollen grain by resuspending the pellet of step (d) in pollen germination medium.

21. The method according to claim 20 in which the flowering plant contains trinucleate pollen.

22. The method according to claim 20 in which the flowering plant is selected from the group consisting of corn, rice, wheat, sugar beet, tomato, clover, tobacco, arabidopsis, soybean, and Brassica species.

23. The method according to claim 20 in which the polyethylene glycol has a molecular weight of at least about 800.

24. The method according to claim 20 in which the salt is selected from the group consisting of sodium chloride, potassium chloride, sodium phosphate, potassium phosphate, and calcium chloride.

25. The method according to claim 20 in which the osmoticum is selected from the group consisting of a sugar or sugar alcohol.

26. The method according to claim 20 in which the sugar or sugar alcohol is selected from the group consisting of dextrose, galactose, glucose, fructose, mannose, ribose, sucrose, glucitol, mannitol, sorbitol, or threitol.

27. The method according to claim 20 in which the aqueous stabilization solution comprises about 5–15% polyethylene glycol, 70–200 mM NaCl, and 5–20% sucrose.

28. The method according to claim 20 in which the aqueous stabilization solution further comprises effective amounts of calcium and boron.

29. The method according to claim 28 in which the calcium is selected from the group consisting of calcium acetate, calcium chloride or calcium nitrate.

30. The method according to claim 28 in which the boron is selected from a group consisting of boric acid or sodium borate.

31. The method according to claim 28 in which the aqueous stabilization solution comprises about 5–15% polyethylene glycol, 70–200 mM NaCl, and 5–20% sucrose, 0.5 mM–5 mM calcium nitrate, 0.3 mM–3 mM borate, and 0.5 mM–5 mM potassium chloride.

32. The method according to claim 20 in which the growth of the pollen tube of the pollen suspended in aqueous stabilization medium of step (c) is suspended for about 1 minute to about 60 minutes.

33. The method according to claim 20 in which the growth of the pollen tube may be resumed by suspending the stabilized pollen in a solution of pollen germination medium.

34. The method according to claim 32 in which the stabilized pollen is suspended in aqueous pollen germination medium comprising an osmoticum, calcium and boron.

35. The method according to claim 34 in which the osmoticum is selected from the group consisting of a sugar or sugar alcohol.

36. The method according to claim 35 in which the sugar or sugar alcohol is selected from the group consisting of dextrose, galactose, glucose, fructose, mannose, ribose, sucrose, glucitol, mannitol, sorbitol or threitol.

37. The method according to claim 34 in which the calcium is selected from the group consisting of calcium acetate, calcium chloride or calcium nitrate.

38. The method according to claim 34 in which the boron is selected from a group containing boric acid and sodium borate.

39. The method according to claim 34 in which the pollen germination medium comprises 5-20% sucrose, 0.5 mM-5 mM calcium nitrate, and 0.3 mM-3 mM sodium borate.

40. The method according to claim 1 in which the flowering plant is a corn plant.

41. The method according to claim 1 in which the flowering plant is a tobacco plant.

* * * * *